United States Patent
Grewe et al.

(10) Patent No.: US 9,681,939 B2
(45) Date of Patent: Jun. 20, 2017

(54) SILANE BONDED MEDICAL DEVICES AND METHOD OF MAKING SAME

(71) Applicants: David Douglas Grewe, West Lafayette, IN (US); Kenneth Aaron Haselby, Battle Ground, IN (US); Keith Milner, West Lafayette, IN (US); Sara Marie Sherman, Lafayette, IN (US)

(72) Inventors: David Douglas Grewe, West Lafayette, IN (US); Kenneth Aaron Haselby, Battle Ground, IN (US); Keith Milner, West Lafayette, IN (US); Sara Marie Sherman, Lafayette, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 572 days.

(21) Appl. No.: 13/675,435

(22) Filed: Nov. 13, 2012

(65) Prior Publication Data

US 2013/0131779 A1  May 23, 2013

Related U.S. Application Data

(60) Provisional application No. 61/561,762, filed on Nov. 18, 2011.

(51) Int. Cl.
 *A61F 2/07* (2013.01)
 *A61L 31/10* (2006.01)
 *A61L 31/02* (2006.01)

(52) U.S. Cl.
 CPC ............ *A61F 2/07* (2013.01); *A61L 31/022* (2013.01); *A61L 31/10* (2013.01); *A61L 2420/02* (2013.01)

(58) Field of Classification Search
 CPC ....................................................... A61F 2/07
 See application file for complete search history.

(56) References Cited

U.S. PATENT DOCUMENTS

| | | | |
|---|---|---|---|
| 3,646,155 | A | 2/1972 | Scott |
| 3,705,911 | A | 12/1972 | Thomson |
| 3,944,574 | A | 3/1976 | Marsden et al. |
| 4,593,071 | A | 6/1986 | Keogh |
| 5,112,919 | A | 5/1992 | Furrer et al. |
| 5,359,111 | A | 10/1994 | Kleyer et al. |
| 6,013,855 | A | 1/2000 | McPherson et al. |
| 6,589,275 | B1 | 7/2003 | Ivancev et al. |
| 6,596,402 | B2 | 7/2003 | Soerens et al. |

(Continued)

FOREIGN PATENT DOCUMENTS

| | | |
|---|---|---|
| GB | 1 536 562 | 12/1978 |
| WO | WO 98/05269 A1 | 2/1998 |
| WO | WO 2010/000478 A1 | 1/2010 |

OTHER PUBLICATIONS

Gelest, Inc., "Silane Coupling Agents: Connecting Across Boundaries", v. 2.0, (2006), p. 1-60.

(Continued)

*Primary Examiner* — Daniel Lee
(74) *Attorney, Agent, or Firm* — Brinks Gilson & Lione

(57) ABSTRACT

A method for bonding a graft material to a support element employing a silane coupling agent, and a medical device obtainable by the method. A medical device including a graft material bound to a support element by a plurality of silane linkages is also described.

16 Claims, 5 Drawing Sheets

(56) References Cited

U.S. PATENT DOCUMENTS

| | | |
|---|---|---|
| 6,706,408 B2 * | 3/2004 | Jelle ............................. 428/447 |
| 6,974,471 B2 | 12/2005 | Van Schie et al. |
| 7,005,493 B2 | 2/2006 | Huang et al. |
| 7,175,652 B2 | 2/2007 | Cook et al. |
| 7,232,459 B2 | 6/2007 | Greenberg et al. |
| 7,294,147 B2 | 11/2007 | Hartley |
| 7,368,163 B2 | 5/2008 | Huang et al. |
| 7,608,100 B2 | 10/2009 | Osborne et al. |
| 7,674,284 B2 | 3/2010 | Melsheimer |
| 7,846,194 B2 | 12/2010 | Hartley et al. |
| 7,914,567 B2 | 3/2011 | Pavcnik et al. |
| 7,927,367 B2 | 4/2011 | Chuter |
| 7,931,932 B2 | 4/2011 | Herrmann et al. |
| 8,002,816 B2 | 8/2011 | Greenberg |
| 2004/0236399 A1 | 11/2004 | Sundar |
| 2005/0147758 A1 * | 7/2005 | Mao et al. ................. 427/372.2 |
| 2005/0222667 A1 * | 10/2005 | Hunt ........................ A61F 2/07 623/1.13 |
| 2006/0093771 A1 | 5/2006 | Rypacek et al. |
| 2007/0056469 A1 | 3/2007 | Van Ooij et al. |
| 2007/0141365 A1 | 6/2007 | Jelle et al. |
| 2010/0247931 A1 | 9/2010 | Al-Lamee et al. |
| 2011/0015090 A1 | 1/2011 | Majeti et al. |
| 2011/0015099 A1 | 1/2011 | Xiong et al. |

OTHER PUBLICATIONS

European Patent Office Communication EP12193069.7-1455, dated Feb. 2, 2015.

* cited by examiner

SILANE BONDED MEDICAL DEVICES AND METHOD OF MAKING SAME

CROSS-REFERENCE TO RELATED APPLICATIONS

This application claims the benefit of U.S. Provisional Patent Application Ser. No. 61/561,762, filed on Nov. 18, 2011, the entire contents of which are incorporated herein by reference.

BACKGROUND

Stent grafts and covered stents are widely used to treat aneurysms, occluded vessels, and restenosis. These devices are generally constructed from a stent and a graft material secured to the stent. In existing stent grafts and covered stents, the graft material is generally secured to the stent by suturing, taping, or stapling. However, these methods require the addition of extra material (e.g., suture thread) and thereby increase the profile of the device and the size of the sheath required to deliver the device. It has been a challenge to develop a method for securing a graft material to a stent without increasing the overall profile of the stent graft device.

SUMMARY

Utilizing the principles of the present invention, a graft material may be secured to a support element by forming a covalent bond between the graft material and the support element. In some embodiments, the covalent bond provides strong adhesion between the graft material and the support element without increasing the overall profile of the device.

In another embodiment, a method is provided for bonding a graft material to a support element. The graft material is placed in contact with the support element in the presence of a silane coupling agent. The graft material, support element, and silane coupling agent are then heated to an effective temperature to bond the graft material to the support element. A medical device manufactured by this method is also provided.

In a yet another embodiment, a medical device including a graft material bound to a support element by a plurality of silane linkages is provided.

Further objects, features, and advantages of the present invention will become apparent from consideration of the following description and the appended claims when taken in connection with the accompanying drawings.

DETAILED DESCRIPTION

The present invention generally relates to a method of bonding a graft material to a support element and a medical device manufactured by said method. The invention also relates to a medical device comprising a graft material bonded to a support element by a silane linkage.

Figure 1:
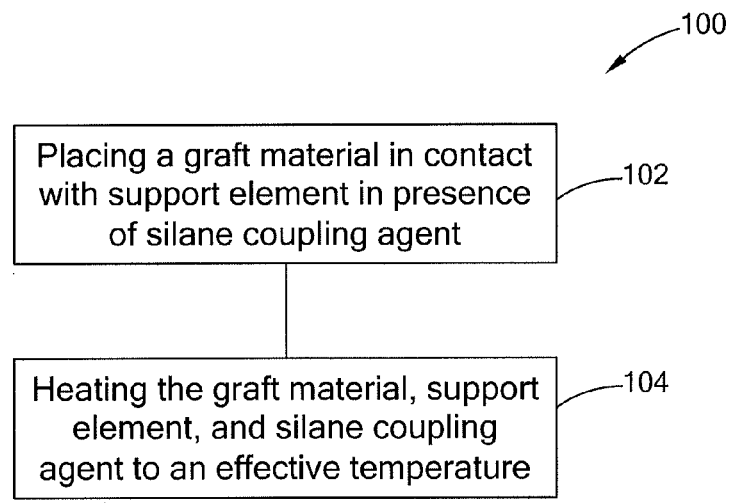
FIG. 1 is a flow chart depicting a method for bonding a graft material to a support element.

Referring to FIG. 1, a method 100 for bonding a graft material to a support element is described. As indicated in box 102, the method 100 involves placing the graft material in contact with the support element in the presence of a silane coupling agent. As indicated in box 104, the method 100 further involves heating the graft material, support element, and silane coupling agent to an effective temperature to bond the graft material to the support element.

As used herein, the term "support element" refers to any component of a medical device that imparts a three-dimensional structure to the device. The support element may be rigid, semi-rigid, flexible, or expandable. In some embodiments, the support element is a component of an implantable medical device, such as a stent.

The support element may be formed from any suitable material. In some embodiments, the support element comprises a metallic material, such as a nickel-titanium alloy (e.g., NITINOL), stainless steel, tantalum, titanium, gold, platinum, inconel, iridium, silver, tungsten, cobalt, chromium, or any other biocompatible metal, alloys of any of these, or any other suitable metallic material. In some embodiments, the support element comprises a nickel-titanium alloy, stainless steel, or a cobalt-chromium alloy. In some embodiments, the support element comprises a nickel-titanium alloy. In some embodiments where the support element comprises a metallic material, the graft material is bound to the metallic material.

As used herein, the term "graft material" broadly refers to any sheet material suitable for covering or encapsulating a support element of a medical device. In some embodiments, the graft material is a pre-formed sheet material that is draped, stretched, wound, or wrapped around or across the surface of the support element. In some embodiments, the graft material is not a coating formed directly on the surface of the support element.

The graft material may be formed from any suitable material and may comprise a single material, a blend of materials, a weave, a laminate, a film, or a composite of two or more materials. In some embodiments, the graft material comprises a polymer material, such as polyethylene, polypropylene, polyethylene terephthalate, expanded polytetrafluoroethylene, polyurethane, or polyetherurethane. In some embodiments, the graft material comprises ultra high molecular weight polyethylene, such as ultra high molecular weight polyethylene having a molecular weight between about 2 million and about 6 million.

As used herein, the term "silane coupling agent" broadly refers to any silicon-containing compound or mixture suitable for bonding a graft material to a support element. In some embodiments, the silane coupling agent is the compound of Formula I, as defined below, or one of the silicon-containing compounds described in U.S. Pat. Nos. 3,705,911; 3,944,574; 5,359,111; 3,646,155; 5,112,919; 6,013,855; 6,596,402; 6,706,408; 7,005,493; 7,931,932; and US Publication Nos. 2007/0056469; 2007/0141365; 2010/0247931; and 2011/0015099; each of which is incorporated herein by reference in its entirety. In some embodiments, the silane coupling agent is a compound of Formula I. In some embodiments, the silane coupling agent is a compound of Formula Ia or Ib, as defined below.

In some embodiments of the method, the silane coupling agent is a compound of formula I:

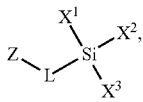

wherein:

$X^1$, $X^2$, and $X^3$ are independently selected from a group consisting of $C_1$-$C_4$ alkoxy, $C_1$-$C_4$ acyloxy, Cl, Br, and I;

L is selected from a group consisting of a bond, a substituted or unsubstituted $C_1$-$C_{10}$ alkanediyl group, and $(CH_2)_n(C_6H_4)(CH_2)_p$, wherein n=an integer between 0 and 4, and p=an integer between 2 and 4; and Z is selected from a group consisting of

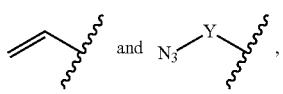

wherein

Y is selected from a group consisting of $SO_2$, C(O), OC(O), and a bond.

In some embodiments of the method, the silane coupling agent is a compound of formula Ia:

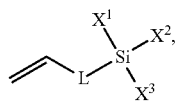

wherein:

$X^1$, $X^2$, and $X^3$ are independently selected from a group consisting of $C_1$-$C_4$ alkoxy, $C_1$-$C_4$ acyloxy, Cl, Br, and I; and L is a bond or a substituted or unsubstituted $C_1$-$C_6$ alkanediyl group.

The compound of formula Ia shall be known as a "vinyl silane coupling agent." In some embodiments, the vinyl silane coupling agent is vinyltrimethoxysilane, vinyltrichlorosilane, vinyltriethoxysilane, vinyltriisopropoxysilane, vinyltri-t-butoxysilane, vinyltriacetoxysilane, vinyltris(isobutoxy)silane, allyltrimethoxysilane, allyltrichlorosilane, hex-5-en-1-yltrichlorosilane, hex-5-en-1-yltriethoxysilane. In some embodiments, the vinyl silane coupling agent is vinyltrimethoxysilane.

In some embodiments of the method, the silane coupling agent is a compound of formula Ib:

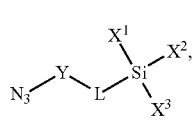

wherein:

$X^1$, $X^2$, and $X^3$ are independently selected from a group consisting of $C_1$-$C_4$ alkoxy, $C_1$-$C_4$ acyloxy, Cl, Br, and I;

Y is selected from a group consisting of $SO_2$, C(O), OC(O), and a bond; and

L is selected from a group consisting of a substituted or unsubstituted $C_1$-$C_{10}$ alkanediyl group, and $(CH_2)_n(C_6H_4)(CH_2)_p$, wherein n=an integer between 0 and 4, and p=an integer between 2 and 4.

In some embodiments, Y is selected from a group consisting of $SO_2$, C(O), and OC(O). In some embodiments, Y is $SO_2$.

The compound of formula Ib shall be known as an "azido silane coupling agent." In some embodiments, the azido silane coupling agent is 6-azidosulfonylhexyltriethoxysilane or 4-(azidosulfonyl)phenethyltrimethoxysilane. In some embodiments, the azido silane coupling agent is 6-azidosulfonylhexyltriethoxysilane.

The term "$C_2$-$C_4$ acyloxy" means acetoxy, propanoyloxy, n-butanoyloxy, or 2-methylpropanoyloxy.

The term "$C_1$-$C_4$ alkoxy" means methoxy, ethoxy, n-propoxy, isopropoxy, n-butoxy, sec-butoxy, neobutoxy, or tert-butoxy.

The term "$C_1$-$C_4$ alkyl" means methyl, ethyl, n-propyl, isopropyl, n-butyl, sec-butyl, neobutyl, or tert-butyl.

The term "alkanediyl group" means any straight-chain aliphatic diradical. An alkanediyl group may have a specified number of carbon atoms (e.g., a "$C_1$-$C_{10}$ alkanediyl group" has between one and 10 carbon atoms). An alkanediyl group may be unsubstituted or may include one or more substitutents selected from a group consisting of $C_1$-$C_4$ alkyl, $C_1$-$C_4$ alkoxy, benzyl, and phenyl.

In the first step of the method of one embodiment, the graft material is placed in contact with the support element in the presence of the silane coupling agent. The graft material, support element, and silane coupling agent may brought together in any order. For example, the silane coupling agent may be applied to the graft material before the graft material is placed in contact with the support element. Alternatively, the silane coupling agent may be applied to the support element before the support element is placed in contact with the graft material. In a second alternative, the graft material may be placed in contact with the support element, and then the silane coupling agent applied to both the graft material and the support element simultaneously.

Regardless of the order in which the graft material, support element, and silane coupling agent are brought together, the silane coupling agent may be dissolved in a solvent and applied to the graft material and/or support element as a solution, i.e., as a "silane coupling agent solution." The silane coupling agent solution may be applied to the graft material and/or support element by any suitable means known in the art. For example, the silane coupling agent solution may be applied by dipping the graft material and/or support element into the silane coupling agent solution, by spraying or brushing the silane coupling agent solution onto the graft material and/or support element, or by any other suitable means. The silane coupling agent solution may be applied to the entire graft material and/or support element, e.g., by submerging the whole device in the solution, or the solution may be applied selectively to discrete locations on the graft material and/or support element. After the silane coupling agent solution is applied to the graft material and/or the support element, the solvent may be allowed to evaporate before the graft material and support element are heated.

The silane coupling agent solution may comprise any suitable solvent. For example, the solvent may be an alcohol, acetone, toluene, methylene chloride, or any other suitable solvent. In some embodiments, the solvent is an alcohol, such as ethanol. In some embodiments, the concentration of the silane coupling agent in the silane coupling agent solution is between about 3% w/v and about 10% w/v, or between about 4% w/v and about 8% w/v, or between about 5% and about 7% w/v. The silane coupling agent solution may be referred to as a "vinyl silane solution" or an "azido silane solution," depending on the nature of the silane coupling agent.

In addition to the silane coupling agent, the silane coupling agent solution may also include a silanol condensation catalyst. Silanol condensation catalysts are known in the art, and any suitable silanol condensation catalyst may be included in the silane coupling agent solution. In some embodiments, the silanol condensation catalyst is added to the silane coupling agent solution immediately before the solution is applied to the graft material and/or support element. Several suitable catalysts are listed in U.S. Pat. No. 3,646,155, the entire contents of which are incorporated herein by reference. In some embodiments, the silanol condensation catalyst is dibutyltin dilaurate.

Where the silane coupling agent is a vinyl silane coupling agent, the silane coupling agent solution (i.e., the vinyl silane solution) may include a radical initiator. In some embodiments, the vinyl silane solution includes a radical initiator and a radical initiator accelerator.

The radical initiator in the vinyl silane solution may be any suitable radical initiator known in the art, such as an organic peroxide, an azo compound, or any other suitable radical initiator. Exemplary organic peroxides include di-t-butylperoxide, dibenzoyl peroxide, dicumyl peroxide, and dibenzyl peroxide. Exemplary azo compounds include azo-bisisobuyronitrile and 1,1'-azobix(cyclohexanecarbonitrile). In some embodiments, the radical initiator is an organic peroxide. In some embodiments, the radical initiator is dibenzyl peroxide or dicumyl peroxide. In some embodiments, the concentration of the radical initiator in the vinyl silane solution is between about 0.001% w/v and about 10% w/v, or between about 0.01% w/v and about 1% w/v, or between about 0.1% w/v and about 0.5% w/v.

The radical initiator accelerator in the vinyl silane solution may be any suitable radical initiator accelerator known in the art, such as an amine or any other suitable radical initiator accelerator. For example, the radical initiator accelerator may be dimethyl amine, trimethyl amine, ethyl amine, diethyl amine, triethyl amine, n-propyl amine, di-n-propyl amine, tri-n-propyl amine, isopropyl amine, diisopropyl amine, triisopropyl amine, n-butyl amine, isobutyl amine, t-butyl amine, di-n-butyl amine, diisobutyl amine, tri-isobutyl amine, pentyl amine, isopentyl amine, diisopentyl amine, hexyl amine, octyl amine, dodecyl amine, lauryl amine, stearyl amine, aminoethanol, diethanol amine, triethanol amine, aminohexanol, ethoxy aminoethane, dimethyl-(2-chloroethyl)amine, 2-ethylhexyl amine, bis-(2-chloroethyl) amine, 2-ethylhexyl amine, bis-(2-ethylhexyl)amine, N-methyl stearylamine, dialkyl amines, ethylene diamine, N,N'-dimethyl ethylene diamine, tetramethyl ethylene diamine, diethylene triamine, permethyl diethylene triamine, triethylene tetramine, tetraethylene pentamine, 1,2-diaminopropane, di-propylene triamine, tripropylene tetramine, 1,4-diamino butane, 1,6-diamino hexane, 4-amino-1-diethyl aminopentane, 2,5-diamino-2,5-dimethyl hexane, trimethyl hexamethylene diamine, N,N-dimethyl aminoethanol, 2-(2-diethylamino ethoxy)ethanol, bis-(2-hydroxyethyl)-oleyl amine, tris-[2-(2-hydroxy-ethoxy)-ethyl] amine, 3-amino-1-propanol, methyl-(3-aminopropyl)ether, ethyl-(3-aminopropyl)ether, 1,4-butane diol-bis(3-amino-propyl ether), 3-dimethylamino-1-propanol, 1-amino-2-propanol, 1-diethylamino-2-propanol, diisopropanol amine, methyl-bis-(2-hydroxypropyl)-amine, tris-(2-hydroxypropyl)amine, 4-amino-2-butanol, 2-amino-2-methylpropanol, 2-amino-2-methyl-propanediol, 2-amino-2-hydroxymethyl-propanediol, 5-diethylamino-2-pentanone, 3-methylamino-propionic acid nitrile, 6-aminohexanoic acid, 11-aminoundecanoic acid, 6-aminohexanoic acid ethyl ester, 11-aminohexanoic acid isopropyl ester, cyclohexyl amine, N-methylcyclohexyl amine, N,N-dimethylcyclohexyl amine, dicyclohexyl amine, N-ethylcyclohexyl amine, N-(2-hydroxyethyl)-cyclohexyl amine, N,N-bis-(2-hydroxyethyl)-cyclohexyl amine, N-(3-aminopropyl)-cyclohexyl amine, aminomethyl cyclohexane, hexahydro toluidine, hexahydro benzylamine, aniline, N-methyl aniline, N,N-dimethyl aniline, N,N-diethyl aniline, N,N-di-propyl aniline, isobutyl aniline, toluidines, diphenyl amine, hydroxyethyl aniline, bis-(hydroxyethyl)aniline, chloro-aniline, aminophenols, aminobenzoic acids and their esters, benzyl amine, dibenzyl amine, tribenzyl amine, methyldibenzyl amine, α-phenylethyl amine, xylidine, diisopropyl aniline, dodecyl aniline, amino naphthalene, N-methyl aminonaphthalene, N,N-dimethyl aminonaphthalene, N,N-dibenzyl naphthalene, diamino cyclohexane, 4,4'-diamino-dicyclohexyl methane, diamino-dimethyl-dicyclohexyl methane, phenylene diamine, xylylene diamine, diamino biphenyl, naphthalene diamines, toluidines, benzidines, 2,2-bis-(aminophenyl)-propane, amino anisoles, amino-thiophenols, aminodiphenyl ethers, amino cresols, morpholine, N-methyl morpholine, N-phenyl morpholine, hydroxyethyl morpholine, N-methylpyrrolidine, pyrrolidine, piperidine, hydroxyethyl piperidine, pyrrols, pyridines, chinolines, indoles, indolenines, carbazoles, pyrazoles, imidazoles, thiazoles, pyrimidines, chinoxalines, amino morpholine, dimorpholine ethane, [2,2,2]-diazabicyclo octane, or any other suitable radical initiator accelerator. In some embodiments, the radical initiator accelerator is N,N-dimethylaniline. In some embodiments, the concentration of the radical initiator accelerator in the vinyl silane solution is between about 0.01% w/v and about 10% w/v, or between about 0.1% w/v and about 2.0% w/v, or between about 0.5% w/v and about 1.0% w/v.

Where the silane coupling agent is an azido silane coupling agent, the silane coupling agent solution (i.e., the azido silane solution) may include a weak acid catalyst. As used herein, a "weak acid catalyst" is an acid having a $pK_a$ between about 3.0 and about 6.0. Exemplary weak acid catalysts include acetic acid, propionic acid, and lactic acid. In some embodiments, the weak acid catalyst is acetic acid.

In the second step of the method of one embodiment, the graft material, support element, and silane coupling agent are heated to an effective temperature to bond the graft material to the support element. The term "effective temperature" means a temperature effective to activate the silane coupling agent to form a bond between the graft material and the support element and may be readily determined by one having ordinary skill in the art. Generally, the effective temperature is below the melting point of the graft material. In some embodiments, the effective temperature is between about 80° C. and about 200° C., or between about 120° C. and about 160° C., or between about 130° C. and about 140° C., or between about 130° C. and about 135° C.

Heating may be accomplished by any suitable means known to those having ordinary skill in the relevant art. For example, heating may be accomplished in an oven, including but not limited to a vacuum oven, a fluidized bath, or an autoclave. In some embodiments where the silane coupling agent is a vinyl silane coupling agent, heating is performed under high humidity conditions. The term "high humidity conditions" means a relative humidity between about 40% and about 100%, or between about 90% and about 100%. In some embodiments, heating is performed in an autoclave under high humidity conditions. In some embodiments where the silane coupling agent is an azido silane coupling agent, heating is performed in a dry oven.

While not intending to be bound by any theory, the vinyl and azido silane coupling agents are believed to create a bond between the graft material and the support element by the mechanisms shown in Schemes 1 and 2, respectively.

When the silane coupling agent is a vinyl silane coupling agent, the bonding is believed to occur by the mechanism As a person having ordinary skill in the art will appreciate, the mechanistic steps in Scheme 1 may occur in a different order without falling outside the scope or spirit of the present invention. For example, the silane substituents $X^1$, $X^2$, and $X^3$ may hydrolyze (Step 4), and the vinyl silane coupling agent of Formula Ia may become bound to the surface of the support element (Step 5), before the vinyl silane coupling agent binds to the graft material (Steps 2 and 3). Other variations in the order of Steps 1-5 are also possible, and all such variations fall within the scope of the present invention.

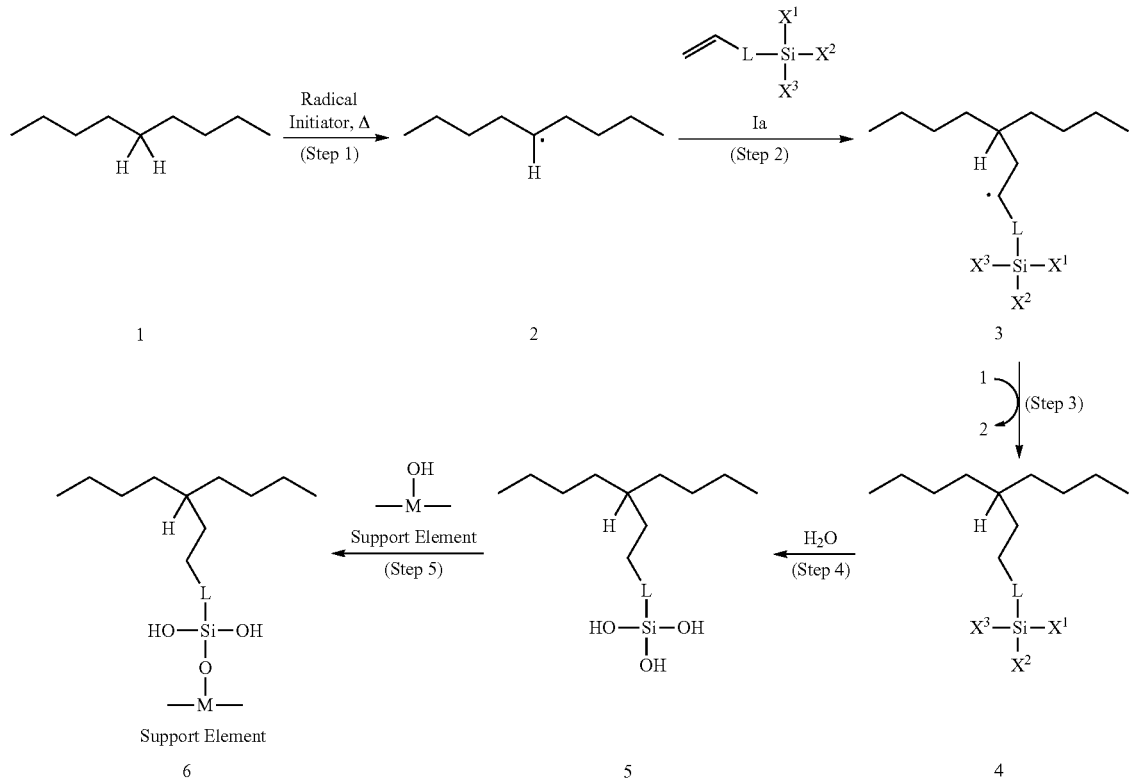

Scheme 1. Proposed Mechanism of Vinyl Silane Mediated Bonding Between Graft Material and Stent shown in Scheme 1. Upon heating, a radical initiator abstracts a hydrogen atom from the graft material 1 to afford a first radical species 2 (Step 1). The first radical species 2 reacts with the double bond of a vinyl silane coupling agent of Formula Ia to afford a second radical species 3 (Step 2). The second radical species 3 abstracts a hydrogen atom from another site on the graft material 1 to afford a first silane-modified graft material 4 and regenerate the first radical species 2 (Step 3). The silane substituents $X^1$, $X^2$, and $X^3$ of the first silane-modified graft material 4 hydrolyze in the presence of water to afford a first silanol-modified graft material 5 (Step 4). The hydroxylsilane moiety of 5 condenses with a metal oxide (M-OH) species on the surface of the support element to afford the first bonded product 6 (Step 5). The condensation reaction of Step 5 may be facilitated by the use of a silanol condensation catalyst, as described above. In addition, the support element may be pretreated with a base, such as aqueous sodium hydroxide, to increase the reactivity of the metal oxide moieties on the surface support element.

When the silane coupling agent is an azido silane coupling agent, the bonding is believed to occur by the mechanism shown in Scheme 2. Upon heating, an azido silane coupling agent of Formula Ib gives off a molecule of nitrogen gas to afford a nitrene intermediate 7 (Step 1). The nitrene moiety of 7 inserts into a C—H bond of the graft material 1 to afford a second silane-modified graft material 8 (Step 2). The silane substituents $X^1$, $X^2$, and $X^3$ of the second silane-modified graft material 8 hydrolyze in the presence of water to afford a second silanol-modified graft material 9 (Step 3). The hydroxylsilane moiety of 9 condenses with a metal oxide (M-OH) species on the surface of the support element to afford the second bonded product 10 (Step 4). As described above, the condensation reaction of Step 4 may be facilitated by the use of a silanol condensation catalyst or by pretreating the support element with a base, such as aqueous sodium hydroxide.

As a person having ordinary skill in the art will appreciate, the mechanistic steps in Scheme 2 may occur in a different order without falling outside the scope or spirit of the present invention. For example, the silane substituents $X^1$, $X^2$, and $X^3$ may hydrolyze (Step 3), and the azido silane coupling agent of Formula Ib may become bound to the surface of the support element (Step 4), before the azido silane coupling agent binds to the graft material (Steps 1 and 2). Other variations in the order of Steps 1-4 are also possible, and all such variations fall within the scope of the present invention.

147; 7,608,100; 7,674,284; 7,846,194; 7,914,567; 7,927,367; and 8,002,816. As a person having ordinary skill in the art will understand, the medical device 200 differs from the devices described in the foregoing publications in that the graft material 204 and the support element 202 are bound by a plurality of silane linkages. In some embodiments, the medical device 200 is an endograft for treating or repairing a thoracic aortic aneurysm (TAA) or abdominal aortic aneurysm (AAA).

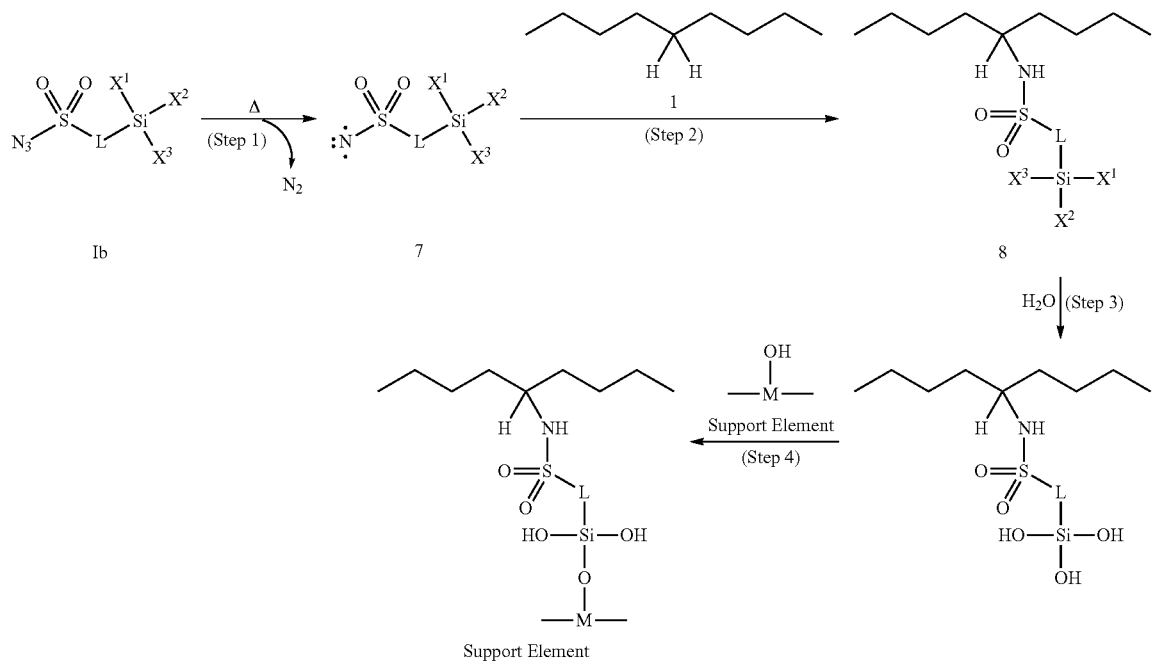

Figure 2:
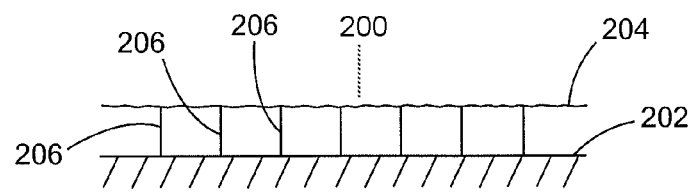
FIG. 2 is a cross-sectional view of a medical device comprising a graft material bound to a support element by a plurality of support elements.

Scheme 2. Proposed Mechanism of Azidosulfonyl Silane Mediated Bonding Between Graft Material and Stent Referring now to FIG. 2, a medical device 200 is described. The medical device 200 comprises a support element 202 and a graft material 204. The graft material 204 is bound to the support element 202 by a plurality of silane linkages 206.

In regard to the medical device 200, the terms "support element" and "graft material" have the same meanings as set forth above. The term "silane linkage" refers to any silicon-containing chemical linkage between a graft material and a support element. In some embodiments, the silane linkage is chemically bound to both the support element and the graft material. In some embodiments, the silane linkage has the chemical structure of species 6 (Scheme 1) or species 10 (Scheme 2). However, the invention is not limited to medical devices in which the silane linkages have these chemical structures.

The medical device 200 may be any medical device in which a graft material 204 is attached, secured, or bonded to a support element 202. In some embodiments, the medical device 200 is an implantable medical device. In some embodiments, the medical device 200 is a stent graft device or covered stent device. For example, the medical device 200 may be constructed in analogy to any of the devices described in the following publications, each of which is incorporated herein by reference in its entirety: U.S. Pat. Nos. 6,589,275; 6,974,471; 7,175,652; 7,232,459; 7,294, A medical device in accordance with the principles of the present invention also includes a medical device manufactured by the method set forth in FIG. 1. Thus, the device is that obtained by (1) placing a graft material in contact with a support element in the presence of a silane coupling agent; and (2) heating the graft material, support element, and silane coupling agent to an effective temperature to bond the graft material to the support element. In some embodiments, the silane coupling agent is a compound of Formula Ia or Formula Ib.

Synthesis of Silane Coupling Agents

The vinyl silane coupling agents and azido silane coupling agents of Formulas Ia and Ib, respectively, are readily prepared from commercially available material using standard synthetic organic chemical transformations familiar to those having ordinary skill in the relevant art.

The vinyl silane coupling agents of Formula Ia may be prepared using one of a number of strategies. For example, where L is a bond or a single $CH_2$ unit, the vinyl silane coupling agents of Formula I are generally commercially available or may be prepared from commercially available material by well-known interconversions of the $X^1$, $X^2$, and $X^3$ groups. Where L is a $C_2$-$C_6$ alkanediyl group, the vinyl silane coupling agents of Formula I may be prepared using the strategy shown in Scheme 3. Namely, silane i(a) is treated with diene i(b) in the presence of a transition metal catalyst to afford the vinyl silane coupling agent of Formula Ia. The box marked "Linker" in diene i(b) corresponds to that portion of the L group in the silane coupling agent of Formula Ia which excludes the two methylene units closest to the silicon atom. The conditions for the reaction shown in Scheme 3 are well-known in the art and have been described in U.S. Pat. No. 5,359,111, the entire contents of which are incorporated herein by reference.

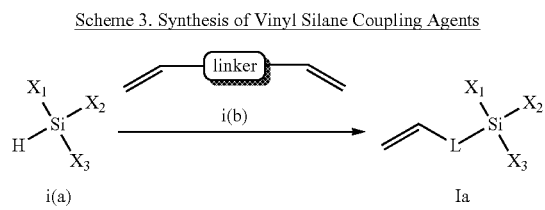

The azido silane coupling agents of Formula Ib may be prepared using one of the strategies shown in Scheme 4. Where Y is $SO_2$, C(O), or OC(O), the coupling agents may be prepared by the strategy shown in Path 1. In step 1, silane ii(a) is treated with alkenyl acid chloride ii(b) in the presence of a platinum catalyst to afford silyl acid chloride ii(c). In step 2, silyl acid chloride ii(c) is treated with sodium azide to afford the azido silane coupling agent of Formula Ib. The conditions for steps 1 and 2 of Path 1 are more fully described in U.S. Pat. No. 3,705,911, the entire contents of which are incorporated herein by reference. Where Y is a bond, the coupling agents may be prepared by the strategy shown in Path 2. Namely, silane ii(a) is treated with vinyl azide ii(d) in the presence of a platinum catalyst to afford the azido silane coupling agent of Formula II. The boxes marked "Linker" in intermediates ii(b) and ii(d) correspond to that portion of the L group in the silane coupling agent of Formula Ib which excludes the two methylene units closest to the silicon atom.

Scheme 4. Synthesis of Azido Silane Coupling Agents

Path 1: Y = $SO_2$, C(O), OC(O)

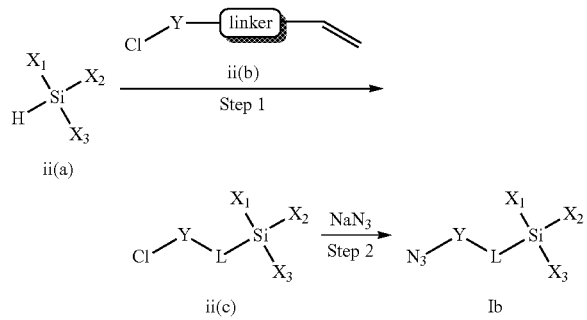

Path 2: Y = a bond

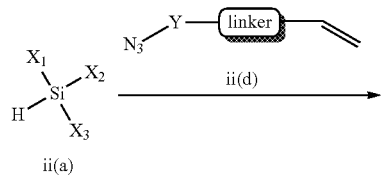

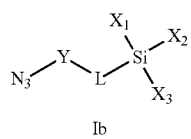

EXAMPLES

The following examples are set forth so that this invention may be more fully understood. These examples are for the purpose of illustration only and are not to be construed as limiting the scope of the invention in any way.

General Procedures

Plasma treatment was performed in a plasma cleaner with a stream of atmospheric pressure oxygen gas. Devices to be treated were placed in the chamber of the plasma cleaner. While not intending to be bound by any theory, radio-frequency energy supplied to electrodes within the chamber of the plasma cleaner is believed to excite the gas in the chamber (in this case, oxygen gas). The excited gas is believed to activate the surface of the devices to accept adhesion.

Lap-shear and T-peel testing were conducted using an INSTRON® 5865 mechanical testing device accordance with standard procedures. Standard procedures for lap shear testing are described in ASTM Standard F2255-05 (2010), "Standard Test Method for Strength Properties of Tissue Adhesives in Lap-Shear by Tension Loading," ASTM International, West Conshohocken, Pa., 2010, DOI: 10.1520/F2255-05R10 (hereinafter "ASTM Standard F2255"). Standards procedures for T-peel testing are described in ASTM Standard F2256-05 (2010), "Standard Test Method for Strength Properties of Tissue Adhesives in T-Peel by Tension Loading," ASTM International, West Conshohocken, Pa., 2010, DOI: 10.1520/F2256-05R10 (hereinafter "ASTM Standard F2256").

6-Azidosulfonylhexyltriethyoxysilane was purchased from Gelest, Inc., Morrisville, Pa. (Catalog Number: SIA0780.0).

Vinyltrimethoxysilane was purchased from Sigma-Aldrich Corp., St. Louis, Mo. (Product Number 235768).

Example 1

Vinyl Silane Mediated Bonding Between Ultra High Molecular Weight Polyethylene Samples and a Nickel-Titanium Alloy Coupon Materials:

1. Electropolished nickel-titanium alloy coupons (2.8 inches×0.25 inches×0.0034 inches) were cleaned by sonication in 1% aqueous LIQUINOX® critical cleaning liquid detergent, followed by rinsing with distilled water and ethanol. The coupons were dried under a stream of nitrogen gas and then plasma treated.

2. Ultra-high molecular weight (UHMW) polyethylene threads (25 denier) and film sheets (0.5 mm thickness) were plasma treated.

3. A vinyl silane solution was prepared by dissolving 5 mL of vinyltrimethoxysilane, 0.243 g of dibenzylperoxide, and 0.777 mL of N,N-dimethylaniline in ethanol. The volume of the solution was adjusted to 100 mL by the addition of additional ethanol.

Procedure:
1. The UHMW polyethylene samples were placed in the vinyl silane solution until the solution began to turn orange (approximately 20 minutes). The samples were then removed from the solution and dried under a stream of nitrogen gas.
2. The dried UHMW polyethylene samples were then placed on nickel-titanium alloy coupons. Where the UHMW polyethylene samples were threads, a single tread was placed on each nickel-titanium alloy coupon. The coupons were heated in an autoclave at 270° F. (132.2° C.) for 120 minutes with a drying cycle of 30 minutes.
3. After removal from the autoclave, the coupons were allowed to dry for approximately 24 hours.
4. Bonding of the UHMW polyethylene samples to the nickel-titanium alloy coupons was analyzed by visual inspection under magnification with a microscope.

Results.

Figure 3:
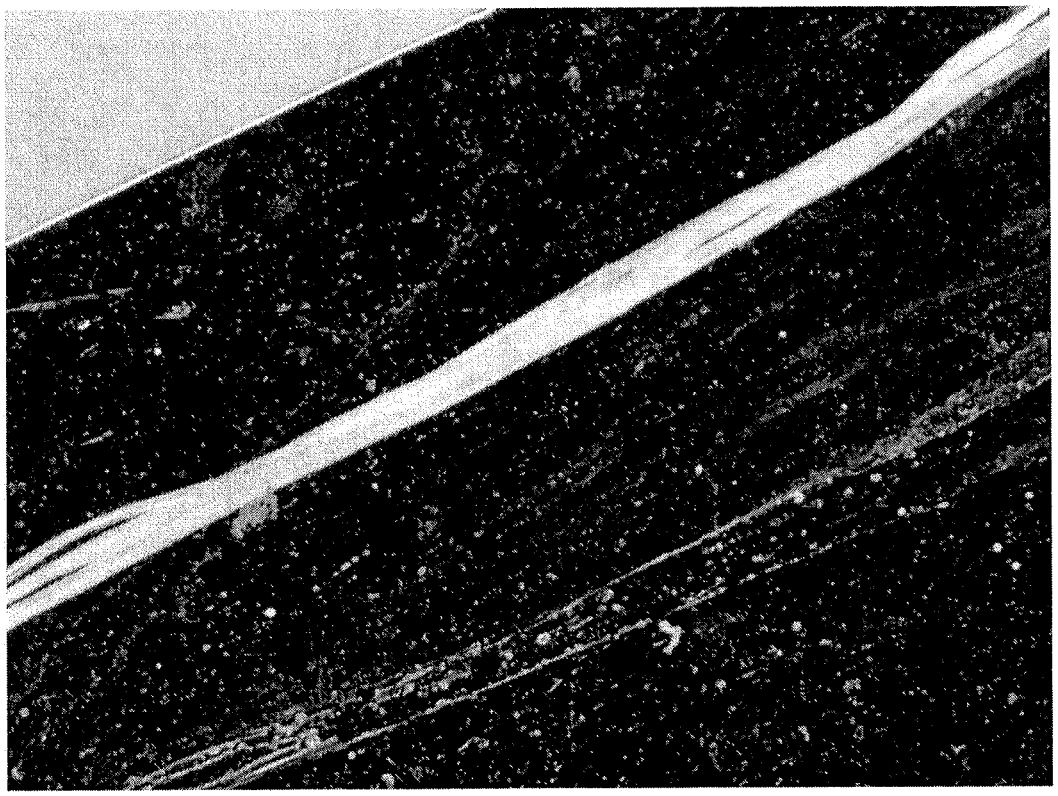
FIG. 3 depicts ultra high molecular weight polyethylene fibers bound to a nickel-titanium alloy coupon.
Figure 4:
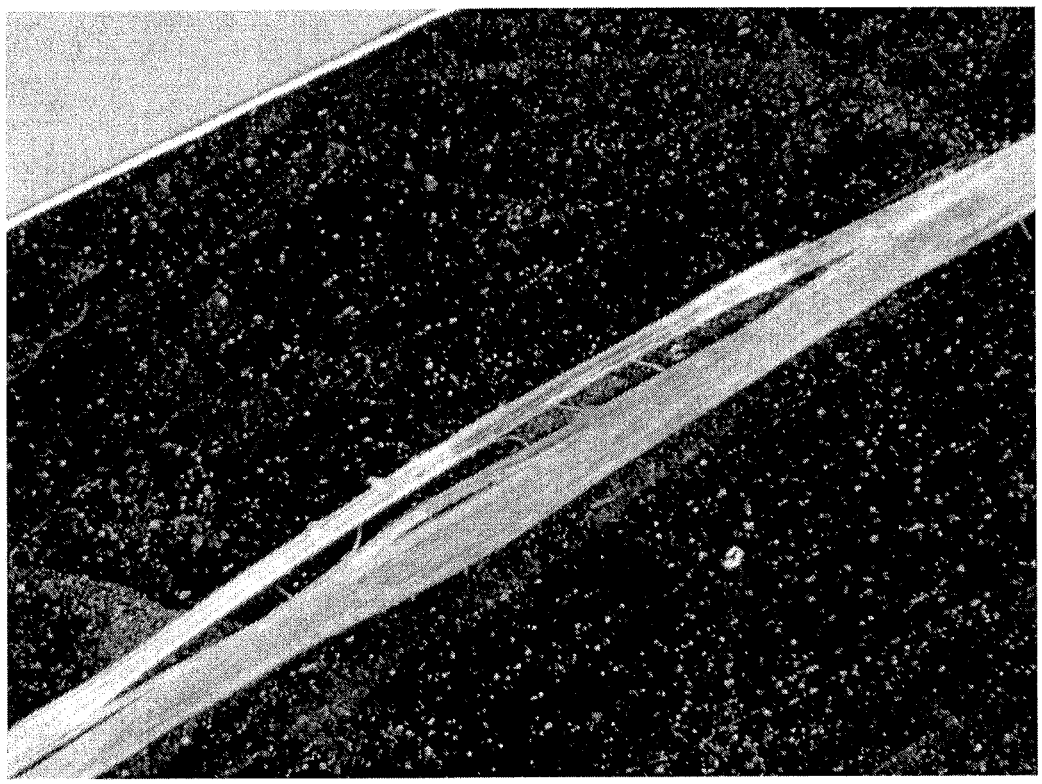
FIG. 4 depicts thread-to thread bonding of ultra high molecular weight polyethylene fibers.

Bonding was observed between the UHMW polyethylene threads and nickel-titanium alloy coupons, and between the threads themselves. The bonding of the threads to the nickel-titanium alloy coupons was evidenced by the difficulty of peeling the threads off of the coupons and by the residue left behind on the coupons when the threads were peeled off of the coupons, as shown in FIG. 3. The thread-to-thread bonding was evidenced by the presence of hair-like projections extending between the threads and by the resistance of the threads to fraying, as shown in FIG. 4. While not intending to be bound by any theory, the observed bonding is believed to involve bonding between titanium oxide species on the nickel-titanium alloy coupon surface and the silicon moiety of the vinyltrimethoxysilane, and between the polyethylene thread and the vinyl group of the vinyltrimethoxysilane. The observed bonding is not believed to involve melting of the polyethylene threads, as the samples were not heated to the melting point of UHMW polyethylene.

Figure 5:
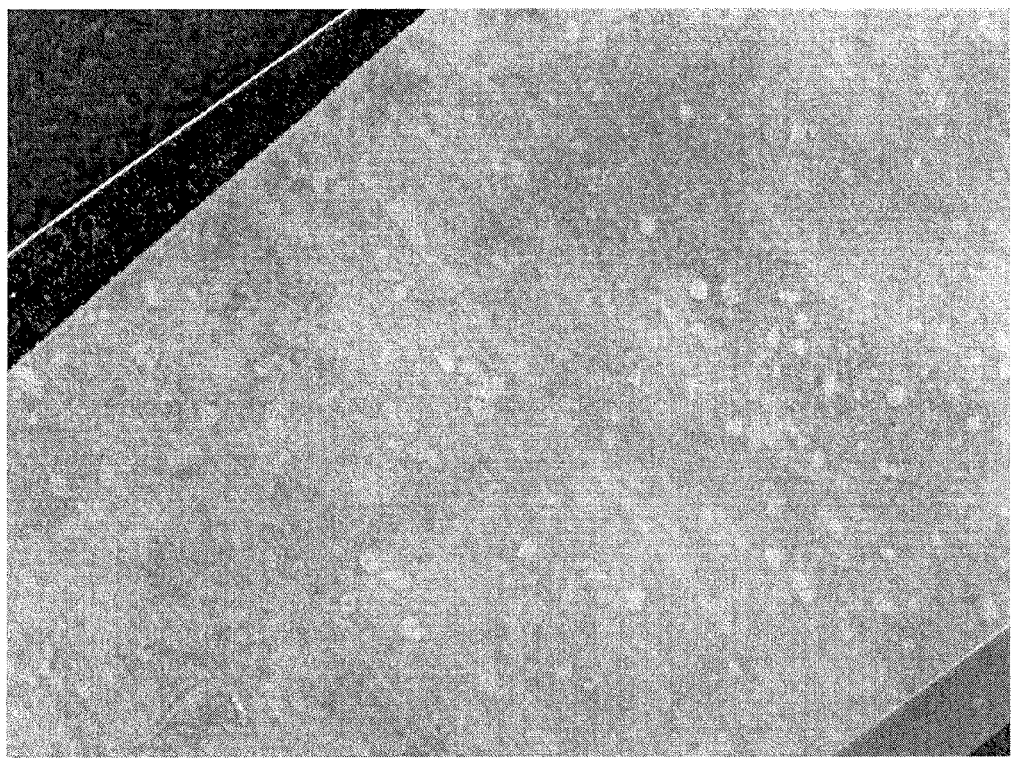
FIG. 5 depicts an ultra high molecular weight polyethylene film bound to a nickel-titanium alloy coupon.

Bonding was also observed between the UHMW polyethylene films and nickel-titanium alloy coupons. This bonding was evidenced by the audible sound detected when the films were peeled off of the coupons and by the residue left behind on the coupons when the films were peeled off of the coupons. A film bound to a nickel-titanium alloy coupon by the method described above is shown in FIG. 5.

Example 2

Azido Silane Mediated Bonding Between Ultra High Molecular Weight Polyethylene Film Sheets and Nickel-Titanium Alloy Coupons Materials:
1. Electropolished nickel-titanium alloy coupons were cleaned by sonication in 1% aqueous LIQUINOX® critical cleaning liquid detergent, followed by rinsing with distilled water and ethanol. The coupons were dried under a stream of nitrogen gas and then plasma treated.
2. UHMW polyethylene film sheets (0.075 mm thickness) were plasma treated.
3. An azido silane solution was prepared by dissolving 6-azidosulfonylhexyltriethoxysilane in ethanol to afford a 5% w/v solution. The solution was stirred constantly prior to and during use.

Procedures:
1. Nickel-titanium alloy coupons were immersed in the azido silane solution for a period of 10 minutes and were then dried under a stream of nitrogen.
2. Experimental samples were prepared by placing an UHMW polyethylene film sheet between two nickel-titanium alloy coupons in the lap shear and T-peel configurations in accordance with ASTM Standard F2255 and ASTM Standard F2256, respectively. Control samples were prepared by placing an UHMW polyethylene film sheet between two nickel-titanium alloy coupons that had not been immersed in the azido silane solution.
3. The nickel-titanium alloy coupons and UHMW polyethylene film sheet of each sample were clamped together to ensure an even distribution of weight and good contact between the coupons and the film sheet.
4. The samples were baked in an oven at 135° C. for 30 minutes.
5. The samples were removed from the oven and allowed to cool to room temperature before the clamps were removed.
6. Lap-shear and T-peel testing were performed on each sample in accordance with ASTM Standards F2255 and F2256, respectively, to determine the strength of the bond between the UHMW polyethylene film sheet and the nickel-titanium alloy coupons. The lap shear testing was conducted using standard methods in accordance with ASTM Standard F2255. The T-peel testing was conducted using standard methods in accordance with ASTM Standard F2256.

Results.

The results of the lap shear testing reveal that the nickel-titanium alloy coupons treated with azido silane formed a strong bond with the UHMW polyethylene film sheets. As shown in Table 1, the bonds in the experimental samples had a significantly higher tensile strength than the bonds in the control samples. These data demonstrate that the azido silane coupling agent played a significant role in the bonding between the nickel-titanium alloy coupons and the UHMW polyethylene film sheet.

TABLE 1

Tensile Strength of Bond Between Nickel-Titanium Alloy Coupons and UHMW Polyethylene Film Sheets as Measured in Lap Shear Test

| Sample | Maximum Tensile Stress (MPa) |
| --- | --- |
| Untreated Nickel-Titanium Alloy Coupons (Control Sample) | 498.50 |
| Nickel-Titanium Alloy Coupons Treated with Azido Silane (Experimental Sample) | 3578.50 |

The results of the T-peel testing also demonstrate that the azido silane coupling reagent effects a bond between the nickel-titanium alloy coupons and the UHMW polyethylene film sheet. As shown in Table 2, the bonds in the experimental samples endured a higher maximum load than the bonds in the control samples.

TABLE 2

Maximum Load of Bond Between Nickel-Titanium Alloy Coupons and UHMW Polyethylene Film Sheets as Measured in T-Peel Test

| Sample | Maximum Load (N) |
| --- | --- |
| Untreated Nickel-Titanium Alloy Coupons (Control Sample) | 0 |
| Nickel-Titanium Alloy Coupons Treated with Azido Silane (Experimental Sample) | 1.232 |

Example 3

Azido Silane Mediated Bonding Between Ultra High Molecular Weight Polyethylene Woven Graft Covering and Nickel-Titanium Alloy Stents Materials:

1. A nickel-titanium alloy wire stent and a cannula cut nickel-titanium alloy stent were cleaned by sonication in 1% aqueous LIQUINOX® critical cleaning liquid detergent, followed by rinsing with distilled water and ethanol. The coupons were dried under a stream of nitrogen gas and then plasma treated.

2. DYNEEMA® UHMW polyethylene tubular woven graft coverings (woven from 25 denier UHMW polyethylene threads).

3. An azido silane solution was prepared by dissolving 6-azidosulfonylhexyltriethoxysilane in ethanol to afford a 5% w/v solution. The solution was stirred constantly prior to and during use.

Procedure:

1. The nickel-titanium alloy wire stent and cannula cut nickel-titanium alloy stent were immersed in the azido silane solution for a period of 30 minutes and were then dried under a stream of nitrogen.

2. The stents were crimped and compressed to fit within the tubular woven graft coverings.

3. The tubular woven graft coverings, with the stents compressed therein, were baked in an oven at 130° C. for 30 minutes.

4. The samples were removed from the oven and allowed to cool to room temperature before handling.

5. Bonding of the tubular graft coverings to the stents was analyzed by visual inspection under magnification with a microscope.

Results.

Bonding was observed between both the nickel-titanium alloy wire stent and the cannula cut nickel-titanium alloy stent and their respective tubular graft coverings. Bonding was confirmed by manual manipulation of the stent and graft covering. More specifically, the apices of the stent were depressed individually toward the longitudinal axis of the stents, relieving the tension of the graft material over the nickel-titanium alloy wires extending between the apices. It was observed that the graft material remained bound to the nickel-titanium alloy wires.

Figure 6A:
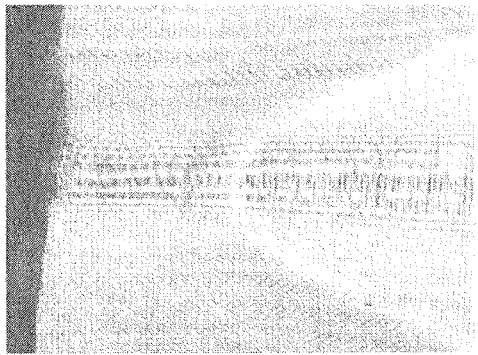
FIGS. 6A-6D depict a stent graft comprising a graft material bonded to a metallic stent.
Figure 6B:
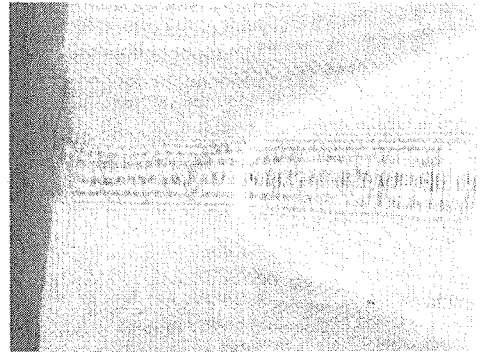
Figure 6C:
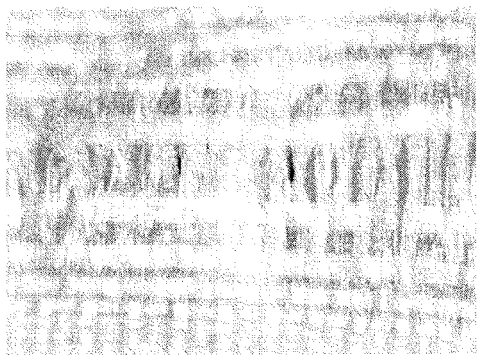
Figure 6D:
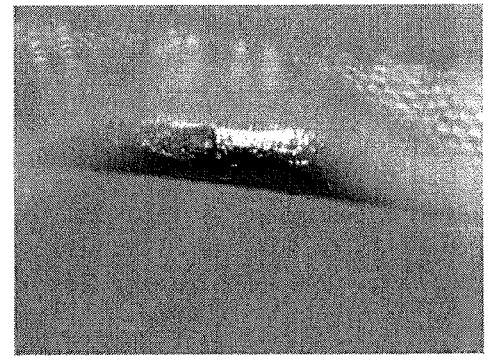

As shown in FIGS. 6A-6D, the tubular graft covering shrunk onto the nickel-titanium alloy wire stent during the baking process. FIG. 6A depicts an unmagnified view of the graft covering stretched over the wires of the stent. FIGS. 6B and 6C depict a woven seam of the graft covering stretched over a wire apex of the stent at 50× and 150× magnification, respectively. FIG. 6D depicts an axial view of a wire apex of the stent having the graft material stretched thereover at 150× magnification. Similar shrinkage of the tubular graft covering onto the cannula cut nickel-titanium alloy stent was also observed. While not intending to be bound by any theory, the shrinkage of the graft coverings is believed to result from a stress release or annealing process, as the baking was performed below the melting temperature of the UHMW polyethylene graft material.

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

The invention claimed is:

1. A method of bonding a sheet of graft material to a metallic support element, the method comprising:
    placing the sheet of graft material in contact with the metallic support element in the presence of a silane coupling agent; and
    heating the graft material, metallic support element, and silane coupling agent to an effective temperature less than a melting point of the graft material to bond the graft material to the metallic support element.

2. The method of claim 1, wherein the graft material comprises a polymer material selected from the group consisting of polyethylene, ultra high molecular weight polyethylene, polypropylene, polyethylene terephthalate, expanded polytetrafluoroethylene, polyurethane, and polyetherurethane.

3. The method of claim 1, wherein the metallic support element comprises a metallic material selected from the group consisting of a nickel-titanium alloy, stainless steel, and a cobalt-chromium alloy, and the graft material is bonded to the metallic material.

4. The method of claim 3, wherein the metallic support element comprises a nickel-titanium alloy.

5. The method of claim 1, wherein the silane coupling agent is a compound of formula Ia:

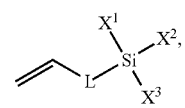

Ia wherein:
    $X^1$, $X^2$, and $X^3$ are independently selected from the group consisting of $C_1$-$C_4$ alkoxy, $C_1$-$C_4$ acyloxy, Cl, Br, and I; and
    L is a bond or a substituted or unsubstituted $C_1$-$C_6$ alkanediyl group.

6. The method of claim 5, wherein the silane coupling agent is vinyltrimethoxysilane.

7. The method of claim 5, wherein said heating the graft material, metallic support element, and silane coupling agent is conducted in the presence of a radical initiator.

8. The method of claim 7, wherein the radical initiator is a peroxide selected from the group consisting of dibenzyl peroxide and dicumyl peroxide.

9. The method of claim 5, wherein said heating the graft material, metallic support element, and silane coupling agent is performed under high humidity conditions.

10. The method of claim 1, wherein the silane coupling agent is a compound of formula Ib:

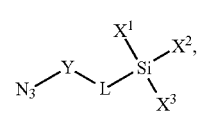

Ib wherein:
X$^1$, X$^2$, and X$^3$ are independently selected from a group consisting of C$_1$-C$_4$ alkoxy, C$_1$-C$_4$ acyloxy, Cl, Br, and I;

Y is selected from the group consisting of SO$_2$, C(O), OC(O), and a bond; and

L is selected from a group consisting of a substituted or unsubstituted alkanediyl group, (CH$_2$)$_n$(C$_6$H$_4$)(CH$_2$)$_p$, wherein n=an integer between 0 and 4, and p=an integer between 2 and 4.

11. The method of claim 10, wherein Y is selected from the group consisting of SO$_2$, C(O), and OC(O).

12. The method of claim 11, wherein Y is SO$_2$.

13. The method of claim 12, wherein the silane coupling agent is 6-azidosulfonylhexyltriethoxysilane.

14. The method of claim 1, wherein said placing the graft material in contact with the metallic support element in the presence of a silane coupling agent comprises:
applying the silane coupling agent to the graft material to form a treated graft material; and
placing the treated graft material in contact with the metallic support element.

15. The method of claim 1, wherein said placing the graft material in contact with the metallic support element in the presence of a silane coupling agent comprises:
applying the silane coupling agent to the metallic support element to form a treated support element; and
placing the graft material in contact with the treated support element.

16. The method of claim 1, wherein said placing the graft material in contact with the metallic support element in the presence of a silane coupling agent comprises;
placing the graft material in contact with the metallic support element; and
applying the silane coupling agent to the graft material and the metallic support element.

* * * * *